(12) United States Patent
Benhamou et al.

(10) Patent No.: US 8,932,596 B2
(45) Date of Patent: Jan. 13, 2015

(54) METHOD OF TREATING EOSINOPHILIC ESOPHAGITIS

(75) Inventors: Pierre-Henri Benhamou, Paris (FR); Lucie Mondoulet, Chatillon (FR)

(73) Assignee: DBV Technologies, Bagneux (FR)

( * ) Notice: Subject to any disclaimer, the term of this patent is extended or adjusted under 35 U.S.C. 154(b) by 77 days.

(21) Appl. No.: 13/413,565

(22) Filed: Mar. 6, 2012

(65) Prior Publication Data

US 2012/0207815 A1 Aug. 16, 2012

Related U.S. Application Data

(63) Continuation of application No. PCT/EP2010/063019, filed on Sep. 6, 2010.

(30) Foreign Application Priority Data

Sep. 7, 2009 (EP) .................................. 09305817

(51) Int. Cl.
| | |
|---|---|
| A61K 38/00 | (2006.01) |
| A61K 39/00 | (2006.01) |
| A61K 39/35 | (2006.01) |
| A61K 39/36 | (2006.01) |
| A61K 39/38 | (2006.01) |
| A61K 9/70 | (2006.01) |
| A61F 13/00 | (2006.01) |
| A61K 35/20 | (2006.01) |
| A61K 36/00 | (2006.01) |
| A61K 36/47 | (2006.01) |
| A61K 36/899 | (2006.01) |
| A61K 35/56 | (2006.01) |
| A61K 35/64 | (2006.01) |

(52) U.S. Cl.
CPC ................. *A61K 39/35* (2013.01); *A61K 35/20* (2013.01); *A61K 36/00* (2013.01); *A61K 36/47* (2013.01); *A61K 36/899* (2013.01); *A61K 35/57* (2013.01); *A61K 35/646* (2013.01); *A61K 9/7023* (2013.01); *A61K 2039/54* (2013.01)
USPC ..................... 424/184.1; 424/275.1; 424/443; 424/449; 514/1.1

(58) Field of Classification Search
None
See application file for complete search history.

(56) References Cited

U.S. PATENT DOCUMENTS

| | | |
|---|---|---|
| 6,800,849 B2 | 10/2004 | Staats |
| 6,864,480 B2 | 3/2005 | Staats |
| 6,925,390 B2 | 8/2005 | Staats |
| 6,969,850 B2 | 11/2005 | Staats |
| 7,618,576 B2 | 11/2009 | Staats |
| 7,635,488 B2 | 12/2009 | Dupont et al. |
| 7,722,897 B2 | 5/2010 | Dupont et al. |
| 7,763,848 B2 | 7/2010 | Staats et al. |
| 8,202,533 B2 | 6/2012 | Mondoulet et al. |
| 8,287,899 B2 | 10/2012 | Dupont |
| 2004/0028727 A1 | 2/2004 | Glenn et al. |
| 2004/0137004 A1 | 7/2004 | Glenn et al. |
| 2006/0002949 A1 | 1/2006 | Glenn et al. |
| 2007/0088248 A1 | 4/2007 | Glenn et al. |
| 2008/0006769 A1 | 1/2008 | Staats |
| 2009/0169602 A1* | 7/2009 | Senti et al. ..................... 424/448 |
| 2010/0222753 A1 | 9/2010 | Dupont et al. |
| 2010/0260821 A1 | 10/2010 | Dupont et al. |
| 2010/0297213 A1 | 11/2010 | Dupont et al. |
| 2010/0310596 A1 | 12/2010 | Ronco et al. |
| 2011/0206659 A1* | 8/2011 | Penn ......................... 424/133.1 |
| 2012/0064144 A1 | 3/2012 | Benhamou et al. |
| 2013/0039958 A1 | 2/2013 | Siegrist et al. |

FOREIGN PATENT DOCUMENTS

| | | |
|---|---|---|
| WO | WO-98/58745 | 12/1998 |
| WO | WO-2007/059979 A2 | 5/2007 |
| WO | WO-2007/012226 A2 | 11/2007 |
| WO | WO-2013/117519 A1 | 8/2013 |

OTHER PUBLICATIONS

Akei, et al., "Epicutaneous Antigen Exposure Primes for Experimental Eosinophilic Esophagitis in Mice," Gastroenterology 2005; 129:985-994.
Mondoulet, et al., "A Model of Eosinophilic Esophagitis (EE) and Villus Atrophy (VA) After Challenge in Mice Sensitized to Peanuts; Improvement by Epicutaneous Immunotherapy (EPIT)," JPGN, vol. 50, Suppl. 2, Jun. 2010, pp. E212.
Dioszeghy et al., "Repeated Applications of Peanut Protein Extracts During Epicutaneous Immunotherapy Induce a Change of Cytokine Response from Th2 to Mixed TH2/TH1 in Sensitized Mice," T. 118, pp. S86.
Mondoulet et al., "Dose-effect of Epicutaneous Immunotherapy (EPIT) for Peanut Allergy," Allergy, Supp., 90, 2009, pp. 83.
Bischoff et al., "Eosinophils and Allergic Diseases of the Gastrointestinal Tract," Best Practice & Research Clinical Gastroenterology, vol. 22, No. 3, 2008, pp. 455-479.
Mondoulet et al., "Epicutaneous Immunotherapy for Peanut Allergy: A Preclinical Study, Food Allergy and Anaphylaxis in Children," 63, Suppl. 88, 2008, pp. 10.
Dioszeghy et al., "Repeated Applications of Peanut Protein Extracts During Epicutaneous Immunotherapy Induce a Change of Cytokine Response from TH2 to Mixed TH2/TH1 in Sensitised Mice," Immunological Basis for the Improvement of Immunotherapy, 64, Suppl. 90, 2009, pp. 225.
Glenn, et al., Transcutaneous immunization: T cell responses and boosting of existing immunity, Vaccine 19:2701-2707 (2001).

* cited by examiner

*Primary Examiner* — Nora Rooney
(74) *Attorney, Agent, or Firm* — Foley & Lardner LLP; Christopher C. Bolten; Nicola A. Pisano

(57) ABSTRACT

The present invention relates to the treatment of EE. More specifically, the invention relates to a new method of treating EE through the epicutaneous route. In particular, the method of the invention comprises applying to the skin of the subject a skin patch device, comprising a composition, under conditions allowing a contact between said composition and the skin. The present invention also relates to the skin patch device and to a use of the skin patch device in the manufacture of a composition for treating eosinophilic esophagitis in a subject.

8 Claims, 4 Drawing Sheets

METHOD OF TREATING EOSINOPHILIC ESOPHAGITIS

CROSS-REFERENCE TO RELATED APPLICATIONS

This application is a continuation under 35 U.S.C. §120 of International Patent Application No. PCT/EP2010/063019, filed on Sep. 6, 2010, which claims the benefit of European Patent Application No. 09305817.0, filed on Sep. 7, 2009, the entire contents of both of which are incorporated herein by reference.

FIELD OF THE INVENTION

The present invention relates to the treatment of eosinophilic esophagitis (EE). More specifically, the invention relates to a new method of treating EE through the epicutaneous route. In particular, the method of the invention comprises applying to the skin of the subject a skin patch device, comprising a composition, under conditions allowing a contact between said composition and the skin. The present invention also relates to the skin patch device and to a use of the skin patch device in the manufacture of a composition for treating eosinophilic esophagitis in a subject.

BACKGROUND OF THE INVENTION

Eosinophilic esophagitis (EE) is characterized by infiltration of the esophagus with eosinophils (1). EE has become increasingly prevalent based on studies in the United States, Switzerland, and Australia (2). For example, 35-fold increase from 2 cases in 1994 to 72 cases in 2003 at The Children's Hospital of Philadelphia (3).

The symptoms of EE have been described as symptoms suggestive of gastroesophageal reflux, which do not respond to gastroesophageal reflux disease (GERD) medications. Other symptoms of EE include dysphagia especially in young adults and failure to thrive in infants (4). The natural history is unknown, but several studies suggest potential progression of untreated disease. Noel et al (5) in a retrospective study of age versus chief complaint found feeding difficulties in the youngest children (median age 2.0 years), vomiting in older children (median age 8.1 years), abdominal pain in adolescents (median age 12.0 years), and dysphagia (mean age 13.4 years) and food impaction (median age 16.8 years) in adults. One possible analysis of this retrospective data is a gradual progression and potential worsening of symptoms from feeding difficulties in infants to strictures and food impaction in adults as a natural history of untreated disease. In the adult population, Straumann et al (6) found no remission in disease in their 11-year follow-up of 30 adults.

The cause of EE is related to allergy. The majority of patients have evidence of food and aeroallergen hypersensitivity, as defined by skin prick test responses, RAST results, or both; however, only a minority have a history of food anaphylaxis, indicating distinct mechanisms compared with classical IgE-mediated mast cell/basophil activation. The immune mechanisms involved in EE are still unclear. It has been established that IL5 and eotaxin enhance the migration of eosinophils to the gut mucosa. Thus, the immune responses in EE are characterized by enhanced production of Th2-associated cytokines in response to both food and environmental allergens. EE and atopic dermatitis (AD) share common features, including eosinophil infiltration, eosinophil degranulation, and squamous epithelial cell hyperplasia, suggesting that common pathogenetic mechanisms may be operational.

EE is defined by the occurrence of high levels of eosinophils (>20-24 eosinophils/high-powered field) in the esophageal mucosa associated with an extensive epithelial hyperplasia. Eosinophils are located both in the proximal and distal esophagus. In addition, esophageal tissues from patients with EE demonstrate thickened mucosa with basal layer hyperplasia and papillary lengthening. EE has been associated with esophageal dismotility, and the cause of the motor disturbances is unclear, but eosinophil activation and degranulation has been postulated as a possible cause. Radiographic and endoscopic studies have shown many findings, including strictures, mucosal rings, ulcerations, whitish papules, and polyps.

The assessment of EE includes an extended allergy evaluation looking for food and aeroallergen sensitization either by means of skin prick tests or RASTs and the exclusion of GERD, as well as other causes of eosinophils in the esophagus. A recent study has suggested that evaluation of food protein sensitization by means of delayed skin patch testing increases the identification of food allergy compared with skin prick testing alone. Of note, the presence of GERD does not exclude the diagnosis of EE or food allergy, demonstrating the importance of a food allergy evaluation in these patients.

The most common foods identified in EE population by the use of prick skin test and atopy patch test are milk, egg, wheat, soja and peanuts.

The most common aero-allergens involved in the EE onset are pollens and House Dust Mite (HDM).

A trial of specific food antigen avoidance is often indicated for patients with atopic EE, and if unsatisfactory or practically difficult (when patients are sensitized to many allergens), a diet consisting of an elemental formula is advocated. Interestingly, it has been shown that an elemental diet frequently improves symptoms and reduces the number of eosinophils in the esophageal biopsy specimens in patients with primary EE (allergic or nonallergic subtypes). Patients on elemental diets frequently require placement of a gastrostomy tube to achieve adequate caloric support. Glucocorticoids (systemic or topical) have also been used with satisfactory results. Systemic steroids are used for acute exacerbations, whereas topical steroids are used to provide long-term control. In a noncontrolled open-label study, topical fluticasone has been shown to decrease levels of eosinophils and CD8+ cells in the proximal and distal esophagus. However, it has been reported that some patients treated with topical fluticasone had esophageal candidiasis.

It appears that EE requires prolonged treatment similar to that for allergic asthma. Although the natural history of EE has not been extensively followed, it is not uncommon for children with EE to have a parent with a long-standing history of esophageal strictures. In fact, in some cases, examination of esophageal biopsy slides from such parents reveals the long-standing presence of EE. Thus, it is likely that chronic EE, if left untreated, can develop into progressive esophageal scaring and dysfunction. The risk for having Barrett's esophagitis, especially in patients with coexisting EE and GERD, has not been determined but is certainly of concern. Additionally, patients with EE are at increased risk for development of other focus of digestive diseases, and thus routine surveillance of the entire gastrointestinal tract by endoscopy is warranted.

Thus, EE is a severe esophageal disease occurring with increasing frequency in children, adolescents and young adults. It is currently treated by food avoidance and corticoids.

Despite the promising results reported with subcutaneous immunotherapy (SCIT), this method is no longer used in food allergy due to the high level of serious side effects or adverse events (AEs). Authors now favor the oral route, i.e., specific oral tolerance induction (SOTI) or oral immunotherapy (OIT), using increasing oral doses and variable time schedules (from one week to at least 1 year or more) or the sublingual technique (SLIT). These methods are promising and their efficacy has been already established. However, in EE, oral route has not been tested. In addition, it could cause a worsening of the EE due to the contact of the esophageal mucosa with the allergen.

Consequently, there is a need for a new method for EE treatment which is safe, efficient and well tolerated by patients.

SUMMARY OF THE INVENTION

The present invention provides a new method of treating EE. More specifically, the invention shows, for the first time, that efficient immunotherapy of EE can be achieved through the epicutaneous route. The present invention shows that an application of the skin patch device according to the invention provokes a very substantial decrease of eosinophils infiltration in esophagus as well as a decrease of the other histological patterns of EE.

In particular, the invention relates to a method of treating eosinophilic esophagitis in a subject, comprising applying to the skin of the subject a skin patch device comprising a composition comprising a substance that causes a cutaneous immune reaction, under conditions allowing a contact between said composition and the skin.

More specifically, the invention relates to a use of a skin patch device comprising a composition comprising a substance that causes a cutaneous immune reaction, in the manufacture of a composition for treating eosinophilic esophagitis in a subject by application of said device on the skin under conditions allowing a contact between said composition and the skin. In a preferred embodiment of the invention, said substance is an allergen, preferably a food or respiratory allergen selected from milk, egg, wheat, soja, peanuts, pollen and House Dust Mite, or a combination thereof.

Another embodiment of the invention relates to an occlusive skin patch device comprising a composition comprising a substance that causes a cutaneous reaction, in dry form, adhered to the patch through electrostatic forces, for treating eosinophilic esophagitis in a subject.

Another particular embodiment of the invention relates to the use of an occlusive skin patch device, as defined above, in the manufacture of a composition for treating eosinophilic esophagitis.

Another preferred embodiment of the invention relates to a method of preventing or reducing the risk of eosinophilic esophagitis in a subject that is allergic, said method comprising applying to the skin of the subject a skin patch device comprising a composition comprising a substance that causes a cutaneous immune reaction, under conditions allowing a contact between said composition and the skin.

The invention also relates to a method of decreasing eosinophilic infiltration in esophagus or gut of an allergic subject, said method comprising applying to the skin of the subject a skin patch device comprising a composition comprising a substance that causes a cutaneous immune reaction, under conditions allowing a contact between said composition and the skin.

The invention also relates to an occlusive skin patch device comprising a composition comprising a combination of at least two allergens selected from milk, egg, wheat, soja, peanuts, pollen and House Dust Mite allergens, preferably in dry form and preferably adhered to the patch through electrostatic forces.

DETAILED DESCRIPTION OF THE INVENTION

Figure 1:
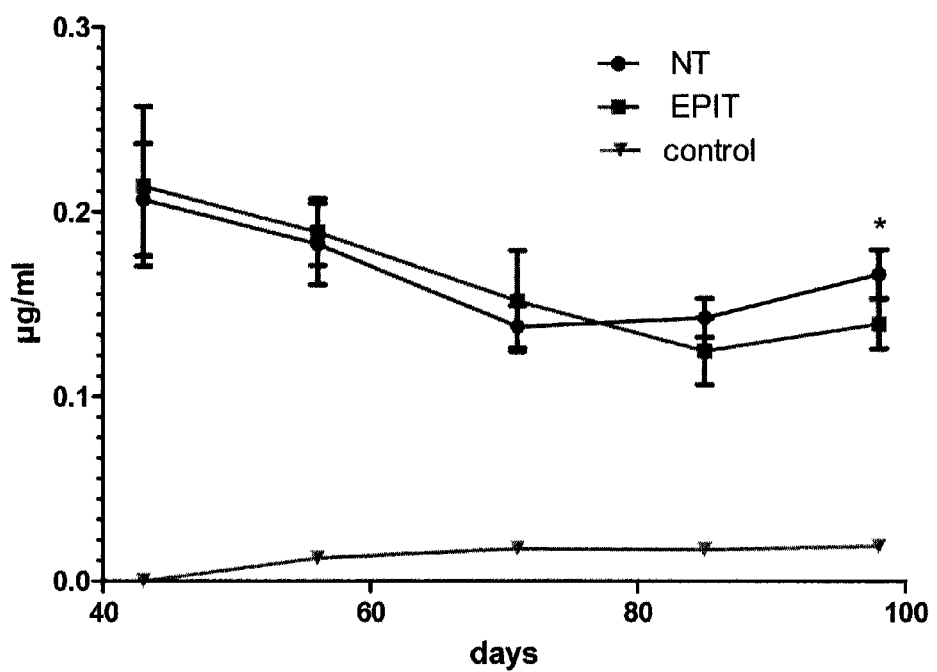
FIG. 1 is a graph that shows the evolution of specific IgE levels in mouse sera during epicutaneous treatment. NT: sensitized non treated mice, EPIT: sensitized treated mice, C: control mice. Mean values are represented and expressed in $\mu g \cdot ml^{-1} \pm SD$.

The present invention relates to a method for treating EE in a subject by epicutaneous immunotherapy.

In particular, the method of the invention relates to a method of treating EE in a subject, said method comprising applying to the skin of the subject a skin patch device comprising a composition comprising a substance that causes a cutaneous immune reaction, under conditions allowing a contact between said composition and the skin.

The invention advantageously shows that such a method causes a substantial decrease of eosinophilic infiltration which is not limited to the esophagus but also other part of the gut such as jejunum, stomach and colon.

More specifically, the invention relates to a use of a skin patch device comprising a composition comprising a substance that causes a cutaneous immune reaction, in the manufacture of a composition for treating eosinophilic esophagitis in a subject.

In a particular embodiment, said subject suffers from hypersensitivity/allergy to food allergen(s) or aero-allergen(s). In a specific embodiment, the subject is allergic to several food allergens and/or aero-allergens.

In a preferred embodiment of the invention, the subject has EE provoked by a combination of food and/or respiratory allergens.

In a particular embodiment, the substance according to the invention is a combination of most frequent allergens involved in EE.

In another embodiment, the invention relates to the method, wherein several (e.g., at least two, three, four or more) allergens are applied on the skin via one or more patch devices, separately, successively or simultaneously.

Another particular object of this invention relates to a patch comprising one or more allergens, selected from milk, egg, wheat, soja, peanuts, pollen and House Dust Mite, preferably a combination of several allergens.

In a particular embodiment, the invention relates to a skin patch device comprising a composition comprising a substance that causes a cutaneous immune reaction, for use in the treatment of eosinophilic esophagitis in a subject by application of said device on the skin under conditions allowing a contact between said composition and the skin.

In a further particular embodiment, the allergen is maintained on the patch through electrostatic forces, wherein said patch is applied to the skin of the subject under conditions allowing a contact between said composition and the skin.

A further embodiment of the present invention resides in the use of an occlusive patch device described above, in the manufacture of a composition for treating EE.

Another particular object of the invention relates to an occlusive skin patch device comprising a composition comprising one or, preferably, a combination of at least two allergens selected from milk, egg, wheat, soja, peanuts, pollen and House Dust Mite allergens, preferably in dry form and preferably adhered to the patch through electrostatic forces, for use in treating EE in a subject.

Another particular object of the invention relates to an occlusive skin patch device comprising a composition comprising a combination of at least three allergens selected from milk, egg, wheat, soja, peanuts, pollen and House Dust Mite allergens, preferably in dry form and preferably adhered to the patch through electrostatic forces.

Another particular object of the invention relates to an occlusive skin patch device comprising a composition comprising a combination of at least four allergens selected from milk, egg, wheat, soja, peanuts, pollen and House Dust Mite allergens, preferably in dry form and preferably adhered to the patch through electrostatic forces.

Another particular object of the invention relates to an occlusive skin patch device comprising a composition comprising a combination of five or more allergens selected from milk, egg, wheat, soja, peanuts, pollen and House Dust Mite allergens, preferably in dry form and preferably adhered to the patch through electrostatic forces.

In a particular embodiment, the invention relates to an occlusive skin patch device comprising an allergen, in dry form, for treating EE.

The present invention provides a new epicutaneous immunotherapy method for treating EE, which comprises (repeatedly) administering to said subject a composition via the epicutaneous route by means of a skin patch device comprising a backing, the periphery of said backing being adapted to create with the skin a hermetically closed chamber, wherein the backing bears on its skin facing side within the chamber said one or more proteins in a dose sufficient to decrease the skin reactivity in said subject following application of the patch device to the skin, said composition being removed from the backing following application of the patch device to the skin and thereafter delivered to the subject via the epicutaneous route, said administration leading, on repetition, to a progressive decrease of a skin reactivity.

In another aspect, the present invention also concerns the use of a skin patch device comprising a backing, the periphery of said backing being adapted to create with the skin a hermetically closed chamber, wherein the backing bears on its skin facing side within the chamber an allergen, in the manufacture of a composition of allergens for treating EE in a subject.

In a particular aspect, in the present invention, the backing bears a combination of protein extracts of the following allergens: milk, egg, peanuts, wheat, soja.

In a particular aspect, in the present invention, the backing bears a combination of protein extracts of milk and wheat.

The invention may be used in any subject, for example animal or human subject, and particularly any human subject, including children and adults.

The immunotherapeutic method of the invention involves the administration of an allergen composition to a subject via the epicutaneous route using particular patch devices, leading to decreasing the eosinophil infiltration in the gut.

As used in this specification, the term "epicutaneous route" means the administration of an allergen to a subject by application of this allergen on the skin. The epicutaneous route does not require the use of a needle, syringe or of any other means to perforate or to alter the integrity of the superficial layer of the epidermis. The allergen is maintained in contact with the skin for period of time and under conditions sufficient to allow the allergen to penetrate into the stratum corneum of the epidermis. Upon repeated and/or prolonged skin applications, the allergen can activate the Langherans cells and the dendritic cells of the derm, leading them to migrate to the lymph nodes and activate immune cells.

The term "treating" includes a reduction of eosinophil infiltration of the gut mucosa in patients, thereby leading to a disappearance of EE. In a particular embodiment, the treatment is preventive and aimed at reducing or preventing the onset or development of EE in a subject, particularly in an allergic subject. Such a preventive treatment generally comprises the repeated application of the device before symptoms of EE, or at early stage thereof.

In another embodiment, the treatment is curative and aimed at reducing or inhibiting the progression of the disease, or at causing a regression thereof.

In a preferred embodiment, the allergen is selected from food allergens and respiratory allergens.

In a preferred embodiment, the allergen composition comprises one or more proteins.

In specific embodiment, the allergen composition is in a liquid form, such as a solution or a dispersion of particles. In that case, effective epicutaneous administration is ensured by migration of the allergen from the liquid phase of the allergen composition to the skin in order to allow the allergen to penetrate into the stratum corneum of the epidermis. In a particular embodiment, the migration of the allergen from the liquid phase of the allergen composition is ensured by diffusion of the allergen through the condensation formed within the hermetically closed chamber, e.g. as a result of perspiration.

In another embodiment, the allergen composition is in a dry form, in particular in a particulate form, obtained, for example, by lyophilisation. The use of proteins in particular dry form is advantageous. Indeed, such particulate allergens may be directly attached to the backing of the device, thereby avoiding any chemical interaction or any reaction which might disturb the immunogenicity of these proteins. Moreover, the use of the particles allows preserving the substance in a suitable packaging, such that there is no longer any need to carry out an extemporaneous preparation. In this case, the epicutaneous administration of allergens held on the backing of the patch may be ensured by dissolution of these allergens in the condensation formed within the hermetically closed chamber.

The allergen composition may further comprise additional components, such as adjuvants.

In an embodiment, the composition used in the present invention is formulated without any adjuvant.

In another embodiment, the allergen composition used in the present invention comprises or is applied with an adjuvant. Within the context of this invention, an adjuvant designates any substance that acts to activate, accelerate, prolong, or enhance antigen-specific immune responses when used in combination with specific antigen. Adjuvant compounds that can be used in combination with composition allergens include mineral salts, such as calcium phosphate, aluminium phosphate, and aluminium hydroxide; immunostimulatory DNA or RNA, such as CpG oligonucleotides; proteins, such as antibodies or Toll-like receptor binding proteins; saponins e.g. QS21; cytokines; muramyl dipeptide derivatives; LPS; MPL and derivatives including 3D-MPL; GM-CSF (Granulocyte-macrophage colony-stimulating factor); imiquimod; colloidal particles; complete or incomplete Freund's adjuvant; Ribi's adjuvant or bacterial toxin e.g. cholera toxin or enterotoxin (LT). The skin patch device used in the method of the invention preferably comprises a backing, the periphery of said backing being adapted to create with the skin a hermetically closed chamber. This backing bears on its skin facing side within the chamber the composition used to decrease the skin reactivity.

Preferably, the periphery of the backing has adhesive properties and forms an airtight joint to create with the skin a hermetically closed chamber.

In a particular embodiment, the composition allergens are maintained on the backing by means of electrostatic and/or Van der Waals forces. This embodiment is particularly suited where the composition allergens are in solid or dry form (e.g., particles), although it may also be used, indirectly, where the allergens are in a liquid form.

Within the context of the present invention, the term "electrostatic force" generally designates any non-covalent force involving electric charges. The term "Van der Waals forces" designates non-covalent forces created between the surface of the backing and the solid allergen, and may be of three kinds: permanent dipoles forces, induced dipoles forces, and London-Van der Waals forces. Electrostatic forces and Van der Waals forces may act separately or together.

In this respect, in a preferred embodiment, the patch device comprises an electrostatic backing. As used herein, the expression "electrostatic backing" denotes any backing made of a material capable of accumulating electrostatic charges and/or generating Van der Waals forces, for example, by rubbing, heating or ionization, and of conserving such charges. The electrostatic backing typically includes a surface with space charges, which may be dispersed uniformly or not. The charges that appear on one side or the other of the surface of the backing may be positive or negative, depending on the material constituting said backing, and on the method used to create the charges. In all cases, the positive or negative charges distributed over the surface of the backing cause forces of attraction on conducting or non-conducting materials, thereby allowing to maintain the allergen. The particles also may be ionized, thereby causing the same type of electrostatic forces of attraction between the particles and the backing.

Examples of materials suitable to provide electrostatic backings are glass or a polymer chosen from the group comprising cellulose plastics (CA, CP), polyethylene (PE), polyethylen terephtalate (PET), polyvinyl chlorides (PVCs), polypropylenes, polystyrenes, polycarbonates, polyacrylics, in particular poly(methyl methacrylate) (PMMA) and fluoropolymers (PTFE for example). The foregoing list is in no way limiting.

The back of the backing may be covered with a label which may be peeled off just before application. This label makes it possible, for instance, to store the composition allergen in the dark when the backing is at least partially translucent.

The intensity of the force between a surface and a particle can be enhanced or lowered by the presence of a thin water film due to the presence of moisture. Generally, the patch is made and kept in a dry place. The moisture shall be low enough to allow the active ingredient to be conserved. The moisture rate can be regulated in order to get the maximum adhesion forces. As discussed above, the use of an electrostatic backing is particularly advantageous where the allergen is in a dry form, e.g., in the form of particles. Furthermore, the particle size may be adjusted by the skilled person to improve the efficiency of electrostatic and/or Van der Waals forces, to maintain particles on the support.

In a specific embodiment, the patch comprises a polymeric or metal coated polymeric backing and the particles of composition allergens are maintained on the backing essentially by means of Van der Waals forces. Preferably, to maintain particles on the support by Van der Waals forces, the average size of the particles is lower than 60 micrometers. In another embodiment, the allergens are maintained on the backing by means of an adhesive coating on the backing. The backing can be completely covered with adhesive material or only in part. Different occlusive backings can be used such as polyethylene or PET films coated with aluminium, or PE, PVC, or PET foams with an adhesive layer (acrylic, silicone, etc.).

The substance in particulate form can be loaded on the backing by means of a spray-drying process, such as an electrospray process as described in the international patent application no WO 2009/095591. An electrospray device uses high voltage to disperse a liquid in the fine aerosol. Allergens dissolved in a solvent are then pulverized on the patch backing where the solvent evaporates, leaving allergens in particles form. The solvent may be, for instance, water or ethanol, according to the desired evaporation time. Other solvents may be chosen by the skilled person. This type of process to apply substances on patch backing allows nano-sized and mono-sized particles with a regular and uniform repartition of particles on the backing. This technique is adapted to any type of patch such as patch with backing comprising insulating polymer, doped polymer or polymer recovered with conductive layer. Preferably, the backing comprises a conductive material.

In another embodiment, the periphery of the backing is covered with a dry hydrophilic polymer, capable of forming an adhesive hydrogel film by contact with the moistured skin (as described in the international patent application no WO 2009/050403). In this embodiment, the skin has to be moistured before the application of the patch. When the hydrogel comes into contact with the moistured skin, the polymer particles absorb the liquid and become adhesive, thereby creating a hermetically closed chamber when the patch is applied on the skin. Examples of such hydrogels include polyvinylpyrolidone, polyacrylate of Na, copolymer ether methyl vinyl and maleic anhydride.

In another particular embodiment, the liquid composition allergen is held on the support of the patch in a reservoir of absorbent material. The composition may consist in an allergen solution or in a dispersion of the allergens, for example in glycerine. The adsorbent material can be made, for example, of cellulose acetate.

The backing may be rigid or flexible, may or may not be hydrophilic, and may or may not be translucent, depending on the constituent material. In the case of glass, the support may be made break-resistant by bonding a sheet of plastic to the glass.

In one embodiment, the backing of the patch contains a transparent zone allowing directly observing and controlling the inflammatory reaction, without necessarily having to remove the patch. Suitable transparent materials include polyethylene film, polyester (polyethylene-terephtalate) film, polycarbonate and every transparent or translucent biocompatible film or material.

In a particular embodiment, the portion of the backing bearing the allergen is not in direct contact with the skin. In this embodiment, the height of the chamber defined by the backing, the periphery of the backing and the skin is in the range of 0.1 mm to 1 mm.

The method of the invention typically involves the repeated application of a device according to the invention to the subject as disclosed above, leading to a progressive decrease of the skin reactivity in the subject.

The specific dose of allergen as well as the number of applications and duration of contact can be adapted by the skilled artisan, depending on the subject, the nature of the allergen preparation, the type of patch device used, etc.

The amount of composition allergens on each patch is typically in the range of 0.1 to 1000 $\mu g/cm^2$ of patch surface, preferably in the range of 20 to 500 $\mu g/cm^2$ of patch surface, more preferably in the range of 20 to 200 $\mu g/cm^2$ of patch surface. The patch surface is in the range of 1 $cm^2$ to 10 $cm^2$, preferably in the range of 1 $cm^2$ to 5 $cm^2$.

For application, the patch devices may be applied directly to the skin, without any pre-treatment, preferably on a hairless part of the body. Alternatively, the skin may be treated prior to application of the device, to disrupt the stratum corneum, to remove hairs or simply to cause hydration of the skin, at the site of contact with the patch device.

As disclosed in the experimental section, the method of the invention results in a progressive decrease of eosinophils in the gut mucosa of the subject.

The present invention also relates to the use of a skin patch device as described above, in the manufacture of a composition for preventing or treating EE in a subject.

The following examples are given for purposes of illustration and not by way of limitation.

EXAMPLES

Methods

Study Design

The feasibility and efficacy of EPIT to treat the eosinophilic esophagitis (EE) was evaluated in a model of mice sensitized to peanut. After a period of sensitization, animals were divided into 2 groups: not treated (NT group) and treated weekly by epicutaneously using the epicutaneous delivery system (EDS) as further described (EPIT), for a total duration of 8 weeks. A control group (C) was also constituted with non-sensitized animals. Blood was sampled for analysis at the beginning and at the end of the experiments, together with histological analyses after oral challenge with peanut allergens.

Animals and Protein Extracts

Four-week-old female BALB/c mice (n=30) purchased from Charles River Laboratories (France) were sensitized to peanut proteins. The use of BALB/c mice as murine model of sensitization to peanut proteins was described in Adel-Patient et al, 2005. This model should reproduce the IgE fine specificity and the symptoms as observed in allergic humans upon challenge. All experiments were performed according to European Community rules of animal care and with permission 92-305 of the French Veterinary Services.

Peanut protein extract (PPE) used was purchased from Greer laboratories (USA).

Protocol of Sensitization

Twenty BALB/c mice received 1 mg of homogenized PPE mixed with 10 µg of Cholera Toxin (CT) on days 1, 6, 12, 18, 24, 30 by means of intra-gastric gavages. Sera were collected from the retro-orbital venous plexus on day 43, centrifuged, and the samples were stored at −20° C. until further assays. Naïve mice were bled on the same days (n=10). Sensitization was monitored by biological parameters as defined above.

Protocol of Treatment (EPIT)

EPIT was performed once a week during 8 weeks as follow:

Mice were anaesthetized intra-peritoneally with ketamine and xylazine and shaved with an electric clipper and depilatory cream. The day after, dermal patch devices with a backing comprising a hydrogel formed with a solution containing 100 µg of PPE, the periphery of said backing being adapted to create with the skin of the mouse a hermetically closed chamber, were placed on the back of the mouse and maintained by a bandage for 48 hours.

Blood samples were taken every 2 weeks during EPIT and at the end of treatment (D98) in order to measure the serological response.

Allergen Food Challenge and Esophagus Sampling

At the end of treatment, mice were exclusively fed with peanut seed during 3 consecutive days. Then, standard food was reintroduced and mice received 50 mg of peanut powder by intra-gastric administration during 3 consecutive days. Then, mice were killed and esophagus were taken and fixed in 10% neutral buffered formalin, embedded in paraffin and cut into 5 µm sections. Slides were prepared and colored with Hemalun Eosin Safran.

Histological Analyses (Eosinophil in the Esophagus)

Colored slides were blind analysed by an anatomo-pathologist certified by ECVP (European College of Veterinary Pathologists). A first descriptive reading was done for each slide then eosinophils were quantified on 6 representative fields. Results were expressed as eosinophils/$mm^2$ tissue area.

Quantification of Specific IgE, IgG1, IgG2a

Blood samples were collected from retro-orbital venous plexus before and during immunotherapy and the plasma were stored at −30° C. until further analyses.

A quantitative ELISA, validated using FDA 2001 guidelines, was used for specific IgE, IgG1 and IgG2a. Briefly, microtiter plates were coated with PPE act at a concentration of 10 µg/ml. Serial dilutions of 100 µl of each serum were dispensed per well and incubated for 24 h at 4° C. An anti-mouse IgG1 or IgG2a antibody labelled with phosphatase alkaline (Serotec, England) was used as a tracer. Reagent (pNPP) (Sigma, France) was used as an enzyme substrate. Specific IgE, IgG1 and IgG2a were quantified by comparison with concentration-response curves obtained with a total IgE, IgG1 or IgG2a assay performed under identical conditions using a solid phase coated with an anti-mouse IgE, IgG or IgG2a antibody (Serotec, England) instead of peanut proteins, which is complementary to tracers. Mouse immunoglobulin standards were obtained from Serotec.

Statistical Analysis

The Graph Pad Software (San Diego, USA) was used for statistical analysis. Serologic data were analysed using analysis of variance (ANOVA) and Dunnett's test when comparing treated mice with controls, or using ANOVA and Tukey's test when comparing all the groups with each other. For eosinophil count, data are expressed as mean±SD. Statistical significance comparing different sets of mice was determined using t-test.

Results

Serological Response

IgE and IgG1: Peanut sensitization was particularly characterized by a production of specific IgE on day 43 as shown in FIG. 1. After EPIT, specific IgE was significantly decreased in EP group (0.139±0.01 µg/ml) compared to NT group (0.166±0.01 µg/ml) ($p<0.05$). Furthermore, during the immunotherapy, no modification of specific IgG1 was observed (Data not shown).

Figure 2:
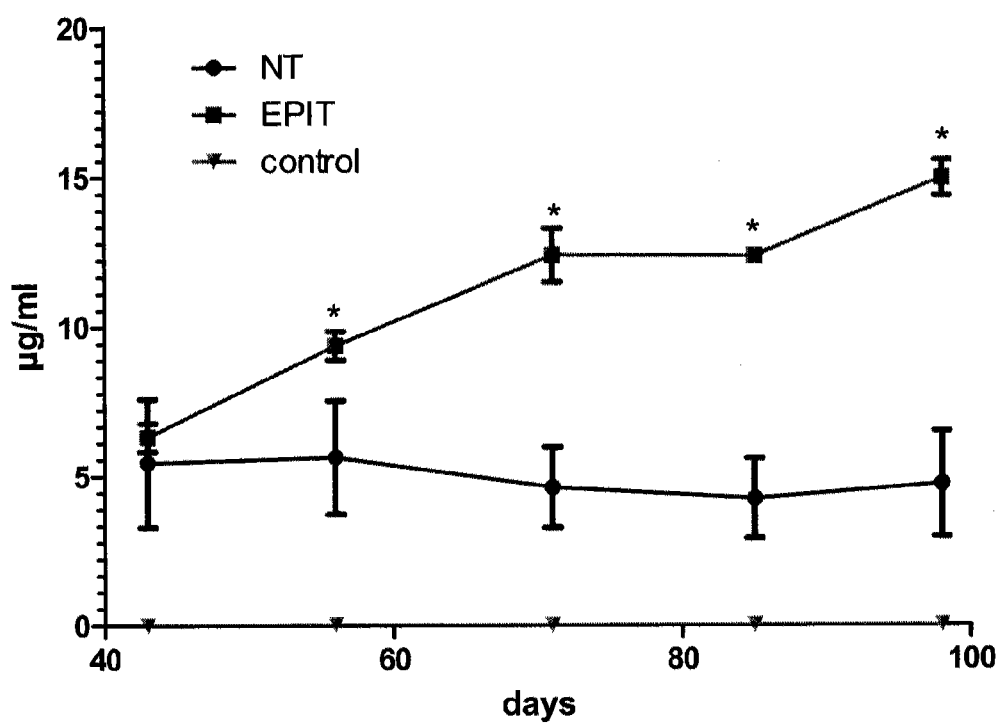
FIG. 2 is a graph that shows the evolution of specific IgG2a levels in mouse sera during epicutaneous treatment. NT: sensitized non treated mice, EPIT: sensitized treated mice, C: control mice. Mean values are represented and expressed in $\mu g \cdot ml^{-1} \pm SD$.

IgG2a: specific IgG2a significantly increased for treated mice after 8 weeks of EPIT (FIG. 2) compared to NT mice (FIG. 2), respectively 14.96±0.60 vs 4.73±1.75 µg/ml ($p<0.05$).

To confirm the immune deviation from a dominant Th2 profile to a balanced Th2/Th1 profile, the ratio IgG1/IgG2a was evaluated for each group. The ratio IgG1/IgG2a decreased only for EP group (from 0.036 to 0.006) not for NT group (from 0.038 to 0.041), showing a boosting of Th1 profile in order to obtain a more balanced Th2/Th1 profile.

Histological Analyses: Eosinophil Quantification

Figure 3:
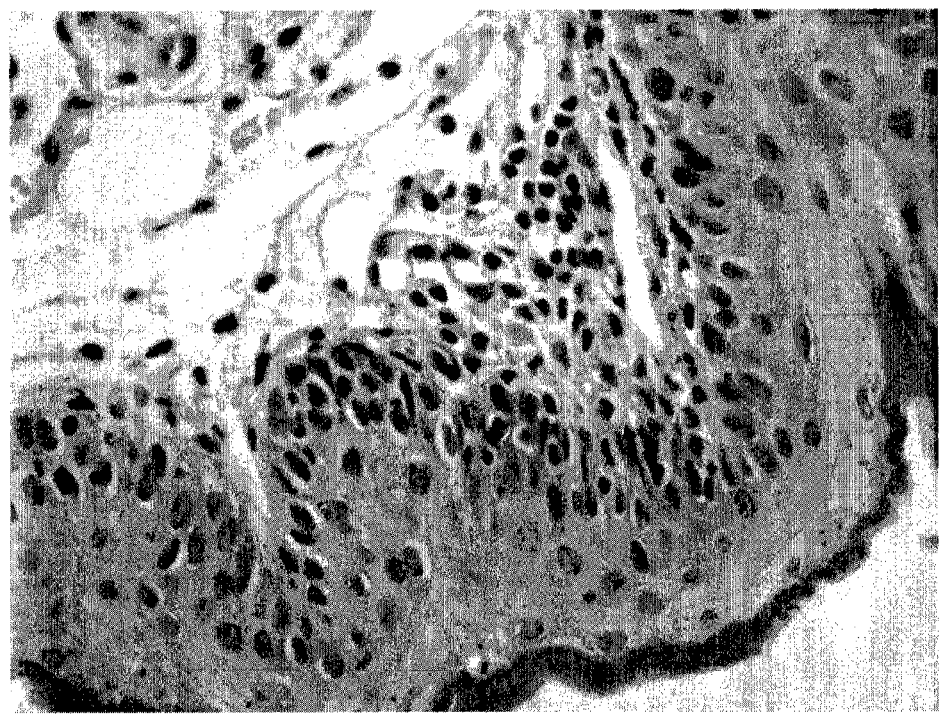
FIG. 3 is a figure that shows a field of the esophagus of a sensitized mouse. Arrow indicates colored eosinophil.

Eosinophilic esophagitis was induced in sensitised NT mice as illustrated in FIG. 3 where an important number of eosinophils could be observed. Eosinophilic infiltration was significantly higher in sensitized NT mice (136±32 eosinophils/mm$^2$) compared to control mice (7±3 eosinophils/mm$^2$) ($p<0.01$) (FIG. 4).

Figure 4:
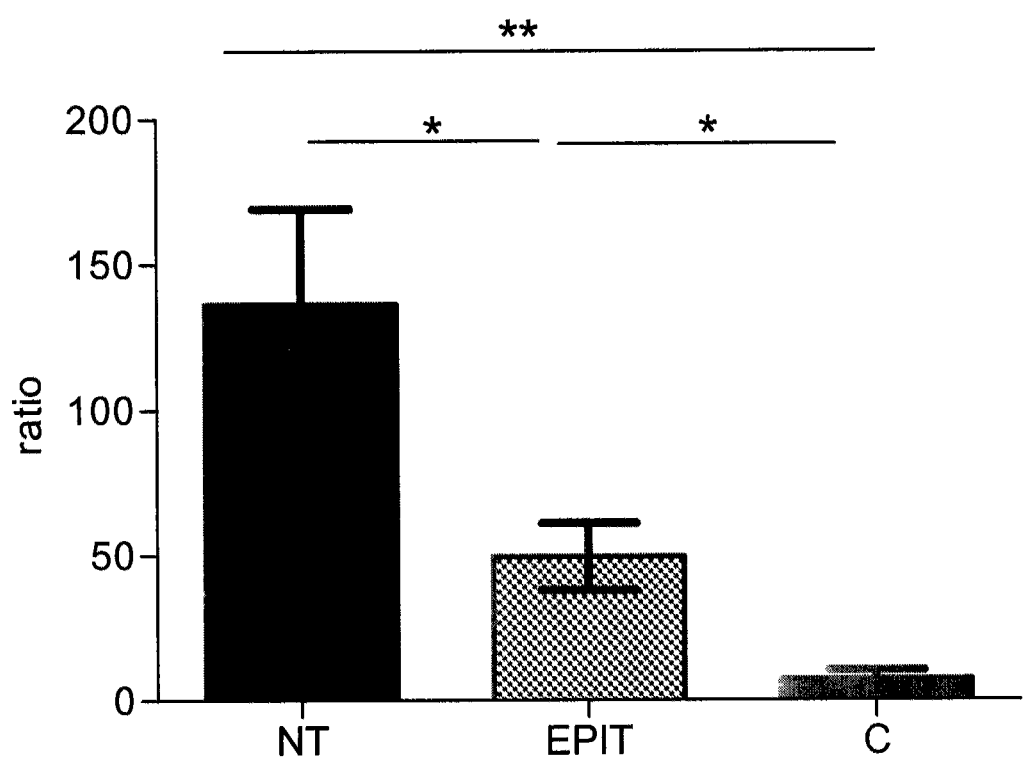
FIG. 4 is a graph representing the quantification of eosinophils per group (NT, EPIT and C). Results are expressed as mean±SD of eosinophils per $mm^2$.

Epicutaneous treatment significantly decreased the number of eosinophils to a mean value of 50±12 eosinophils/mm$^2$ ($p<0.05$) (FIG. 4).

Conclusion

Epicutaneous treatment leading to an immune deviation from a dominant Th2 profile to a rebalanced Th2/Th1 profile seems efficient to prevent eosinophilic esophagitis in a preclinical model of mice sensitized to peanut.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

References

1. Furuta G T, Liacouras C A, Collins M H, et al. Gastroenterology 2007; 133:1342-1363.
2. Cherian S, Smith N M, Forbes D A. Arch Dis Child 2006; 91:1000-1004.
3. Liacouras C A, Spergel J M, Ruchelli E, et al. Clin Gastroenterol Hepatol 2005; 3:1198-1206.
4. Spergel, Jonathan M; Brown-Whitehorn, et al. J Pediatr Gastroenterol Nutr. 2009; 48:30-36.
5. Noel R J, Putnam P E, Rothenberg M E. N Engl J Med 2004; 351:940-941.
6. Straumann A, Spichtin H P, Grize L, et al. Gastroenterology 2003; 125:1660-1669.
7. Rothenberg M. J Clin allergy Immunol 2004; 113:11-28.

The invention claimed is:

1. A method of treating a food-induced eosinophilic esophagitis in a subject, said eosinophilic esophagitis being characterized by an eosinophilic infiltration in the subject, the method comprising epicutaneously applying to the skin of the subject having eosinophilic infiltration a non-perforating skin patch device comprising a composition comprising, as the only active ingredient, a food allergen under conditions allowing contact between said composition and the skin, and in an amount sufficient to cause a decrease of eosinophilic infiltration in an esophagus or gut of the subject, said application resulting in a treatment of said eosinophilic esophagitis.

2. The method of claim 1, wherein said subject suffers from allergy to one or more food allergens.

3. The method of claim 1, wherein the food allergen is selected from the group consisting of milk, egg, wheat, soja, and peanuts.

4. The method of claim 1, wherein more than one allergen is epicutaneously applied on the skin via one or more patch devices, separately, successively or simultaneously.

5. The method of claim 1, wherein the composition is in dry form.

6. The method of claim 1, wherein said method involves a repeated application of the skin patch device.

7. The method of claim 1, wherein said composition further contains a pharmaceutically acceptable carrier.

8. A method of decreasing eosinophilic infiltration in an esophagus or gut of a subject having eosinophilic infiltration, said method comprising epicutaneously applying to the skin of the subject a non-perforating skin patch device comprising a composition comprising, as the only active ingredient, a food allergen under conditions allowing a contact between said composition and the skin, said application resulting in a decrease of eosinophilic infiltration in the esophagus or gut.

* * * * *